United States Patent [19]

Kraft et al.

[11] Patent Number: 4,689,303

[45] Date of Patent: Aug. 25, 1987

[54] CONTROLLED CIRCULATION INCUBATOR

[75] Inventors: Thomas L. Kraft; James W. Meador, both of Houston, Tex.

[73] Assignee: KVM Engineering, Inc., Houston, Tex.

[21] Appl. No.: 832,997

[22] Filed: Feb. 26, 1986

[51] Int. Cl.⁴ .......................... C12M 1/38; F24H 3/04
[52] U.S. Cl. .................................... 435/290; 435/287;
 435/809; 126/2 A; 236/3; 219/400; 219/218;
 219/366; 219/369
[58] Field of Search ............... 435/287, 290, 317, 809;
 237/3, 4, 14, 15; 236/15 BR, 15 BF, 2, 3;
 126/39 C, 396, 21 A, 21 R, 275 E, 275 R, 273
 R, 332, 337 R, 337 A, 339; 219/400, 218, 366,
 369, 370, 371

[56] References Cited

U.S. PATENT DOCUMENTS

| | | | |
|---|---|---|---|
| 1,145,054 | 7/1915 | Boekel et al. | 237/14 X |
| 1,507,719 | 9/1924 | Ritchie | 126/237 R |
| 2,561,517 | 7/1951 | Ladge | 126/237 R X |
| 2,906,620 | 9/1959 | Jung | 126/273 |
| 3,056,553 | 10/1962 | Hazen et al. | 236/3 |
| 3,634,651 | 1/1972 | Siegel et al. | 236/3 X |
| 3,658,047 | 4/1972 | Happel | 126/337 R X |
| 4,269,169 | 5/1981 | Guibert | 126/21 A X |

Primary Examiner—Larry Jones
Attorney, Agent, or Firm—Tim L. Burgess

[57] ABSTRACT

Described herein is a controlled circulation incubator device having a plurality of plate receiving trays held by a tray bracket. Heated air is circulated by a blower and heater assembly around the trays held by the tray bracket and the temperature of the flowing heated air is sensed by a thermister included in a temperature controller circuit. The termister is coupled in a circuit so that its resistance determines the amount of heating provided by the heater portion of the blower and heater assembly. Each of the trays have a front lid and a back lip and the plurality of trays are offset from one another within the confines of the incubator device. The angle of the back lip and the amount of offset are selected so that each of the back lips are positioned in a generally planar surface. This causes the front lip, which extend at a slight angle from the receiving trays, to extend into the circulating air stream and air is forced between adjacent trays to heat the contents held by the trays. At the backside of the trays a low pressure area appears, further forcing air across the trays. The package of the incubator is fabricated of metal to promote heat loss so that the heating means can more accurately control the temperature. A variable resistor is included to allow different temperatures to be selected.

13 Claims, 4 Drawing Figures

CONTROLLED CIRCULATION INCUBATOR

In any clinical microbiology or immunology laboratory, a common device used by researchers and technicians is the incubator. Typically, a culture is placed on a microplate, petridish or other type of plate and maintained at a constant temperature in order for the culture to grow.

In most clinical applications, the reactions normally occur at 37 degrees centigrade. However, in some applications, such as hepatitis testing, the optimum incubation temperature will be 42 degrees centigrade. In fact, any temperature from room temperature up to 50 degrees centigrade may be used in different testing procedures.

In the past, microplates have been incubated in large, generally floor standing incubators, It would be desirable to have a smaller portable incubator which can fit on the benchtop and which can hold different types of plates at controllable and precise temperatures.

In most incubators one of the most difficult tasks is to maintain an extremely constant temperature. In the past this had been done by using highly insulated devices with precision thermostats used as the temperature controlling apparatus. Such devices were both expensive and bulky and did not easily lend themselves to being controlled to provide different temperatures.

In accordance with one aspect of this invention there is provided a controlled circulation incubator device for incubating a group of plates at a constant temperature comprising a plurality of plate receiving means each having a generally planar surface for receiving at least one plate. Each plate receiving means has a front lip at an angle between 135 and 170 degrees with respect to the planar surface and a back lip at an angle between 100 and 135 degrees with respect to the planar surface. In addition, the incubator device includes bracket means for holding a plurality of plate receiving means offset in the front to back direction from one another by an angle substantially the same as the angle of the back lip. Further, the device includes blower and heater means for blowing heated air in a flow path around the plate receiving means and bracket means. The flow path is along the back of the plate receiving means and then over the top of the bracket means and thereafter along the front of the plate receiving means, whereby a low pressure area is created at the back lip of each plate receiving means and some of the air flows from the front lip to the back lip above each plate recieving means. Finally, the device includes sensor means positioned in the flow path of the air remote from between the plate receiving means, whereby a low pressure area is created at the back lip of each plate receiving means and some of the air flows from the front lip to the back lip above each plate receiving means. Finally, the device includes sensor means positioned in the flow path of the air remote from between the plate receiving means for sensing the temperature of the air flowing thereby and for controlling the blower and heater means to maintain the temperature of the air constant.

One preferred embodiment of the subject inventio nis hereafter described with specific reference being made to the following Figures, in which.

Figure 1:
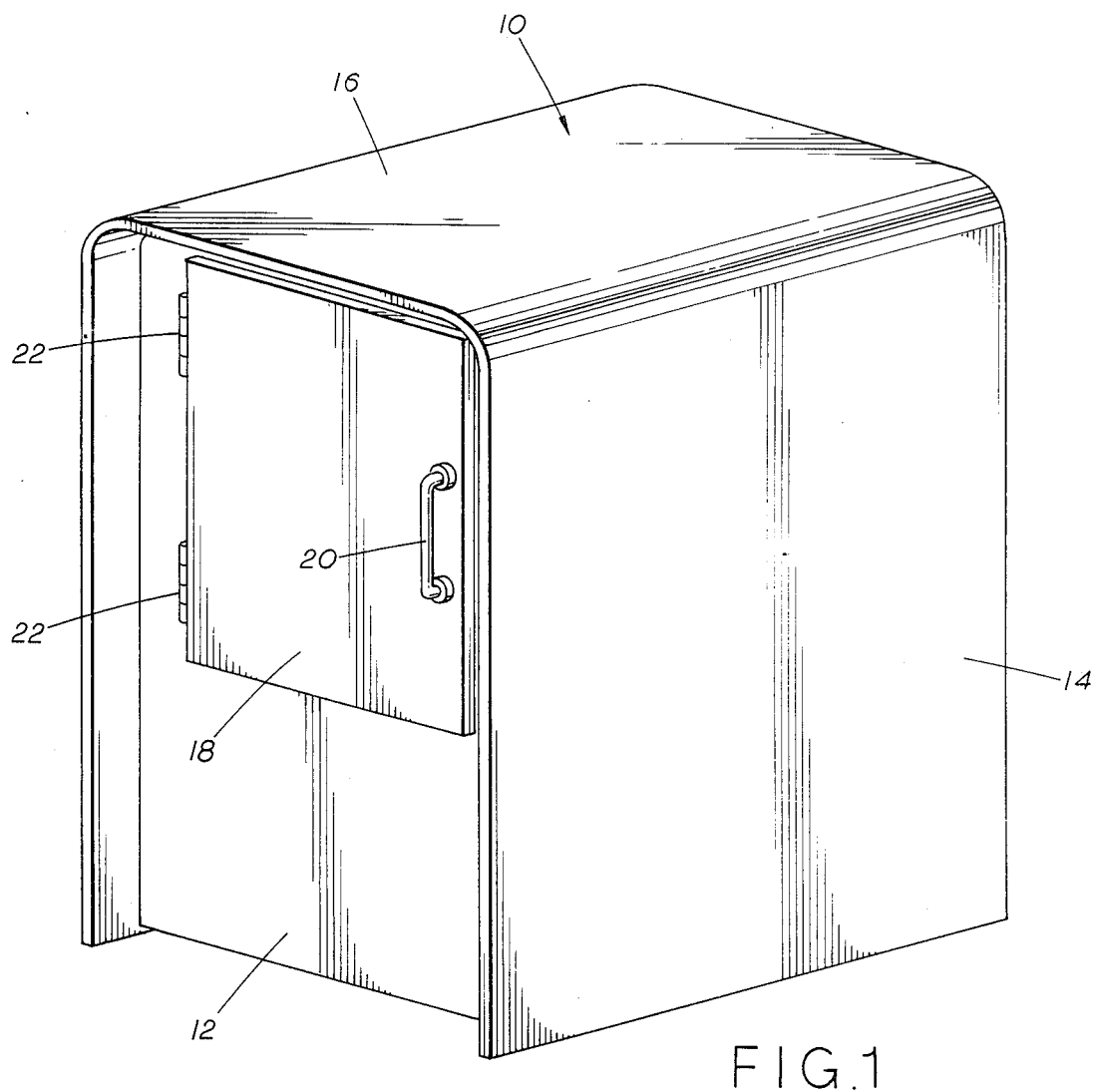
FIG. 1 shows a perspective view of the controlled circulation incubator device of the subject invention.

Referring now to FIG. 1, the controlled circulation incubator device 10 of the subject invention is shown. As seen in FIG. 1, incubator device 10 includes a front 12, a right side 14 and a top 16. A door 18 is positioned over front 12 and covers approximately the upper two-thirds thereof. Door 18 includes a handle 20 for opening and closing door 18 as it rotates around a pair of hinge 22 pins attaching door 18 to front 12.

Figure 3:
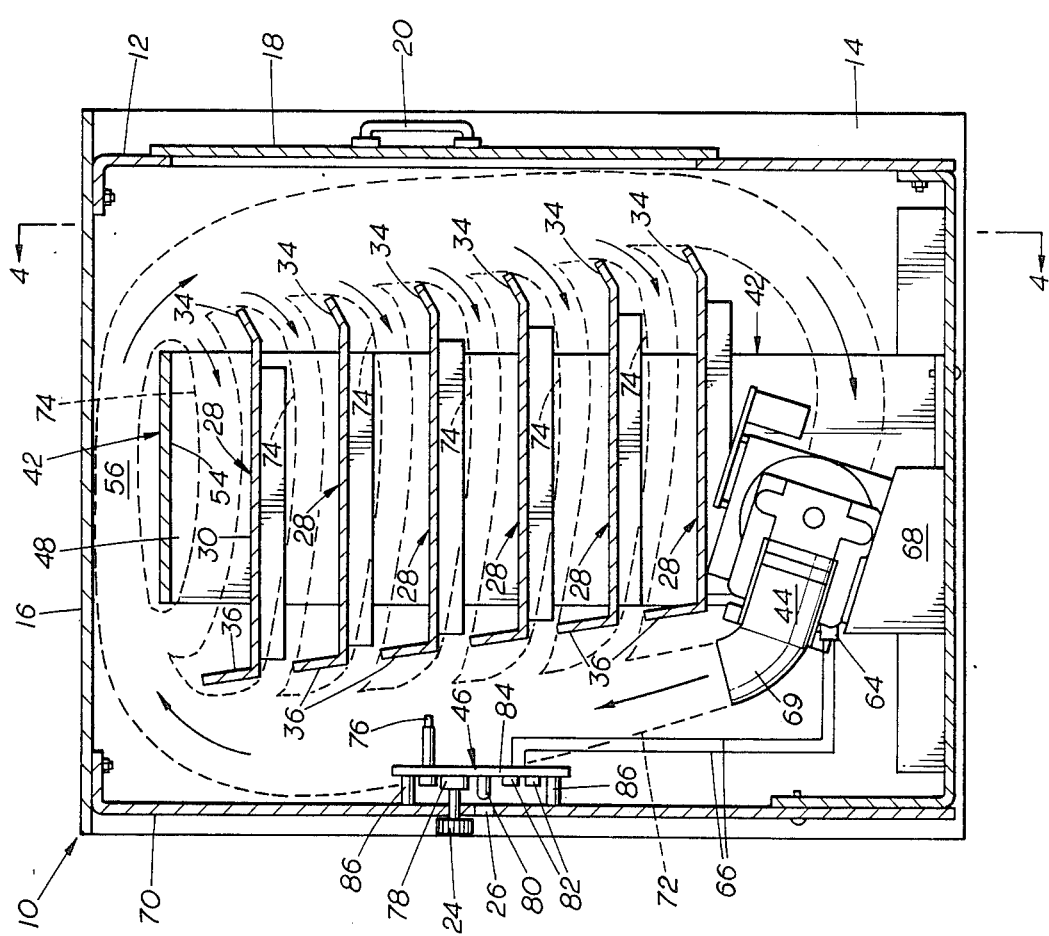
FIG. 3 shows a side view, with the left side removed, of the incubator shown in FIG. 1.

In addition, on the back 70 of device 10, as seen in FIG. 3, a temperature control knob 24 is provided, which can be rotated to set the temperature within device 10 to any desired amount between room temperature and 50 degrees centigrade. Further, the back of device 10 has a viewing hole 26 so that the duty cycle of the heating element within device 10 may be observed. Behind hole 26 is a bulb 80 which is illuminated each time the heater, included within incubator 10, receives current to heat the air flowing therethrough. This will be described in more detail with respect to FIGS. 3 and 4.

Figure 2:
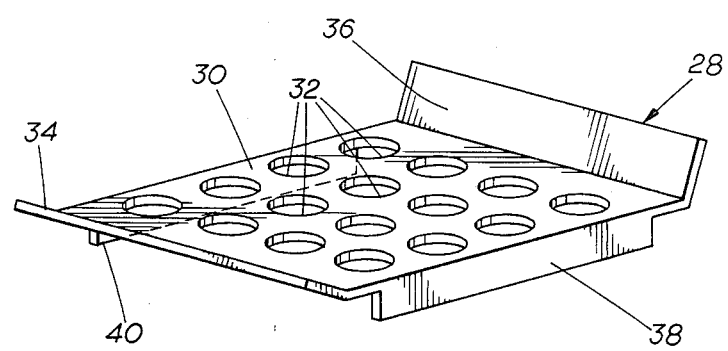
FIG. 2 shows a perspective view of one of the plate receiving means included within the incubator shown in FIG. 1.

Referring now to FIG. 2, one of the plate receiving trays 28 included within the confines of incubator device 10 of FIG. 1 is shown. Within controlled circulation incubator device 10 are a plurality, such as six, of trays similar to tray 28. These are shown in side and front views in FIGS. 3 and 4. Each of the trays 28 are generally positioned so that access thereto may be had through door 18.

Tray 28 includes a receiving surface 30 having a plurality of receiving openings 32 therein. Surface 30 is generally a flat, planar surface and each of the openings 32 may be generally round or square in shape and adapted to receiving a microplate or other type of plate used in microbiology, immunology or other similar type analysis.

The front of tray 28 has a front lip 34 extending therefrom and the back side of surface 30 has a back lip 36 extending therefrom. Front lip 34 extends upward at an angle typically between 135 and 175 degrees. For example, the angle between surface 30 and front lip 34 may be 170 degrees. Back lip 36, on the other hand, is at a much sharper angle with respect to surface 30 than is front lip 34. For example, back lip 36 may be positioned at an angle typically between 100 and 135 degrees with respect to surface 30. More specifically, back lip 36 may be positioned at an angle of 108 degrees with respect to the plane of surface 30. As will be explained hereafter with respect to FIG. 3, the exact angle between back lip 36 and surface 30 is determined by the amount of front to back offset desired between adjacent plates within device 10 and the direction of air flow.

Finally, plate receiving tray 28 includes a left side attaching plate 38 and a right side attaching plate 40, both extending downward from surface 30 on the left and right sides of tray 28. As will be seen hereafter with respect to FIGS. 3 and 4, attaching plates 38 and 40 are used for attaching tray 28 to a bracket within incubator device 10.

Figure 4:
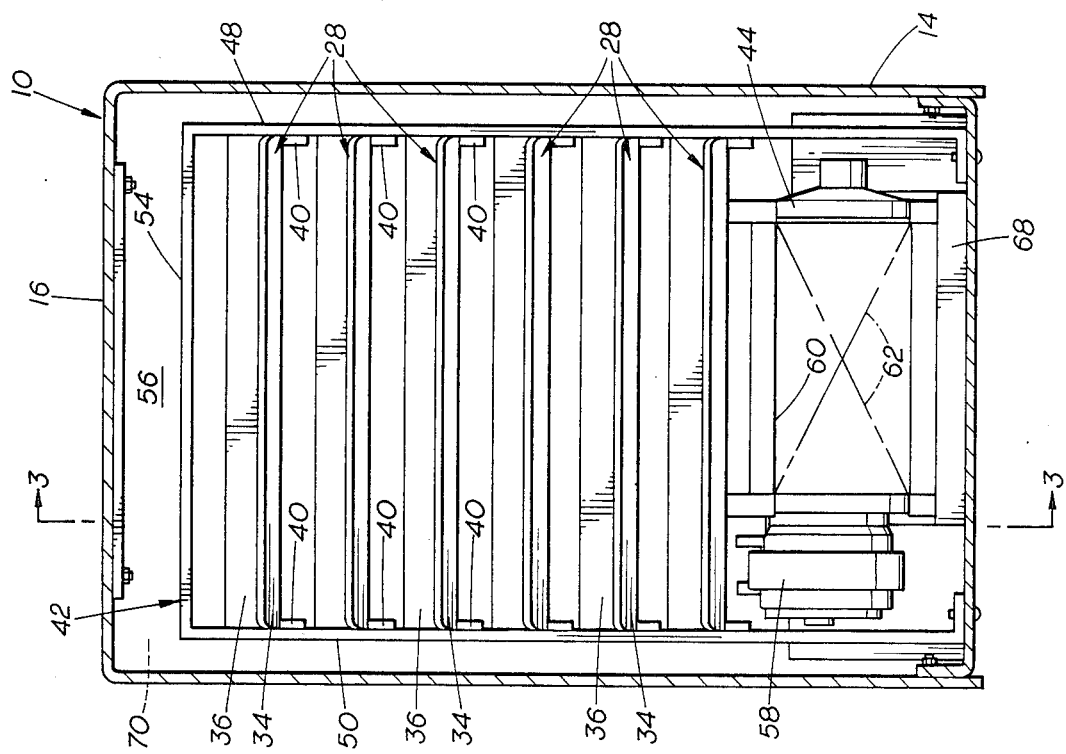
FIG. 4 shows a front view, with the front removed of the incubator shown in FIG. 1.

Referring now to FIGS. 3 and 4, the manner in which the plurality of trays 28 are affixed within incubator device 10, so that the plates can be placed on each of the trays 28 to be incubated at a constant temperature, will now be described. The principle components within incubator device 10 are tray bracket 42, blower and heater assembly 44, and temperature controller circuit 46. It should be noted that circuit 46 is only shown in FIG. 3. Generally, tray bracket 42 holds six different plate receiving trays 28, each offset slightly from the other in the manner to be described in more detail hereafter. Blower and heater assembly 44 includes a fan which receives cooler air at its intake (on the right side in FIG. 3), heats the air internally and blows out warmer air from the left side in FIG. 3. Temperature controller circuit 46 senses the air flow from the blower and heater assembly 44 and provides a voltage to the heater portion of assembly 44 to control the amount of heating of the inlet air passing therethrough based on the temperature sensed.

Reference is now made to tray bracket 42 which is generally an inverted U-shaped bracket having a width equal to the distance between left side attaching plate 38 and right side attaching plate 40 showin in FIG. 2. Each of the two attaching plates 38 and 40 may be spot welded to the sides 48 and 50 of bracket 42. For example, three spot welds 52 may be made on each of the plates 38 and 40 to attach it to one of the sides 48 or 50 of bracket 41. As an alternative these tray brackets 28 may be mechanically attached to bracket 42 and made removeable by the user so that taller items may be incubated. The width of bracket 42 is only slightly less than the side to side width of incubator 10 and the depth of bracket 10 is approximately one-third the front to back depth of incubator 10. The height of bracket 42 is such that its bottom is secured to the bottom of container 10 and its top 54 is positioned below top 16 of incubator device 10 to form a channel 56 therebetween.

Each of the six plate receiving trays 28 attached to bracket 42 are offset in the front to back direction with respect to one another by a slight amount. As air moves over the top of the bracket 42, it is directed downward, essentially parallel to door 18. The offset of the fronts of the trays 48 permits air to be directed between the six tray brackets 28, in turn. Most air goes into the top tray 28, which has the smallest pressure differential at the back of all the trays 28. The high flow of air offsets the lower differential. For the lower trays 28, there is decreasing air volumes directed between the trays 28. However, the back pressure differentials increase for the lower trays 28 and the offsets and angles are all combined to produce constant and uniform air flow over all the trays 28 being incubated. This consistency eliminates gradients and creates uniformity of temperature and evaporation. Thus, uniform and predictable circulation of the air permits device 10 to attain its temperature a shorter time than the prior art devices, such as in approximately three minutes. Also, the circulation is such as to permit predictable control of temperature even with the door open.

Once the amount of the offset is determined, the angle of back lip 36 is selected so that each of the back lips 36 are aligned in the same plane with respect to one another. One example is where the trays 28 are separated by 1.3 inches, the angle of back lip 36 with respect to surface 30 is 108 degrees, and a 0.2 inch offset between adjacent ones of the plate receiving trays 28 is provided. The offset is such that the top tray 28 is furtherest from the front 12 of incubator 10. The length of back lip 36 is selected so that it extends upward by at least one half the distance between adjacent trays 28, so that an air constriction exists.

Blower and heater assembly 44 is positioned below the trays 28 and includes a motor 58 which rotates to force pre-heated air through a chamber 60 after being heated by a heating element 62, schematically shown in FIG. 4. An electrical connector 64 is positioned on blower and heater assembly 44 and is adapted to receive cabling 66 from temperature controller circuit 46. The signals in the cable 66 are applied through connector 64 to control the amount of heating provided by heating element 62. Blower and heater assembly 44 is mounted on a support 68 at an angle facing upward towards the back 70 of incubator device 10 and includes a direction vent 69 at the air exit side. In this manner, the air is directed along an air stream 72 upwards along back 70 and through channel 56 around and downward along front 12 of incubator device 10. The general flow of the air forming air stream 72 within incubator device 10 is shown by the dashed lines in FIG. 2.

Because of the offset between the various plate receiving trays 28, as the air moves upward along the plane in which the back lips 36 are positioned, a low pressure area is created behind lips 36. Further, as the air moves downward along front 12, air is directed between adjacent trays 28 by front lips 34. This causes an air stream 74 to additionally be provided from the front side of each tray 28 to the back side of that tray 28 through the constriction formed by back lip 36. The tray air stream 74 provides a constant heat to the plates placed on tray 28.

The temperature controller circuit 46 includes a thermistor 76, a variable resistor 78, to which is attached knob 24, and neon lamp 80 positioned in alignment with opening 26. In addition, these and other components 82 are attached to a circuit board 84 which is held away from front 12 by posts 86. Thermister 76 is positioned to be in air stream 72 and will provide a resistance dependent upon the temperature of the air in air stream 72. This resistance, in conjunction with the setting of knob 24 and the other components 82 on circuit board 84, cause electric signals to be provided over cable 66 to the heating element 62 within assembly 44 to control the amount of heat provided thereby. The duty cycle of the on/off or greater/or lower heating may be monitored by turning neon lamp 80 on and off. The manner of designing and interconnecting the various elements of controller circuit 46 is well known in the art and will not be described in detail herein.

The outer casing forming incubator device 10 is generally constructed of a good heat conductive material such as aluminum or steel. This type of construction not only provides strength to incubator device 10, but also is desirable in order to maintain the constant temperature control by heating the air provided through blower and heater assembly 44. In order for assembly 44 to cycle the heater on and off and maintain good temperature control, it is necessary that a certain amount of heat be lost from within the incubator device 10. Unless this occurs, the air will be continually recirculated without additional heating and certain cold spots will appear within incubator device 10.

As can be seen, the various elements forming the packaging of incubator 10 are generally flat or bent metal panels which are coupled together by various bolts in a known manner.

What is claimed is:

1. A controlled circulation incubator device for incubating a group of containers at a constant temperature comprising:
  an enclosure;
  a plurality of container receiving means having a generally planar surface for receiving at least one container, each said receiving means having a front lip and a back lip, said backlip having an angle selected between 100 and 135 degrees with respect to said planar surface;
  sidewall bracket means within said enclosure for laterally holding said receiving means spaced apart within sidewalls and substantially parallel to and offset from one another at a predetermined stagger in the front to back direction to produce a plurality of stepped ductways between adjacent receiving means, said back lip of each receiving means having a distance between the distal margin of such back lip and the intersection of the back lip to said planar surface sufficient with respect to the spacing between the receiving means next adjacent the back lip to define a slot aperture between the said distal margin and said next adjacent plate receiving means effective during air circulation to produce a zone of lower pressure at said aperture than at the ductway entrance leading thereto;
  blower and heater means for blowing heated air within said enclosure in a flow path generally transverse to the front to back orientation of said receiving means and generally parallel to and along the back of said receiving means for return circulation along the stepped fronts of said receiving means, whereby a low pressure area is created at said slot apertures and some of said air flows from said front lips through said ductways to exhaust through said slot aperture; and
  sensor means positioned in the flow path of said air remote from between said receiving means for sensing the temperature of the air flowing thereby and for controlling said blower and heater means to maintain the temperature of said air constant.

2. The invention acocrding to claim 1 wherein said sensor means is a thermistor and the resistance of said thermistor controls the amount of heating provided by said blower and heater means.

3. The invention according to claim 2 wherein said sensor further includes a variable resistor settable to control the temperature within said incubator device.

4. The device of claim 1 in which said enclosure includes vertical front and back walls, each said receiving means is essentially normal to the vertical, and each said receiving means is set back from the receiving means below it in a predetermined pattern such that (a) the spacing and horizontal cross-sectional area between the enclosure back wall and each said back lip progressively decreses vertically from the lowermost to the uppermost of said plurality of receiving means to provide an upwardly tapering flow path at the back of said enclosure such that a zone of lowest pressure in said back flow-path is located adjacent the back lip of the uppermost receiving means, and (b) the spacing and horizontal cross-sectional area between the enclosure front wall and each of said front lips progressively increases vertically from the lowermost to the uppermost of said plurality of receiving means to demarcate a downwardly tapering front flow-path in said enclosure, whereby a zone of lowest pressure in said front flow-path is located adjacent the front of the lowermost receiving means.

5. The device of claim 1 in which said distance between the distal margin of said back lip and the intersection of said back lip to said planar surface is at least one-half the distance separating adjacent ones of the plate receiving means.

6. The device of claim 5 in which said receiving means are of substantially equal front-to-back dimension.

7. The device of claim 5 in which the angles of said back lips are substantially uniform.

8. The device of claim 7 the plurality of receiving means are offset from one another by an angle substantially the same as the angle of said back lip.

9. The device of claim 5 in which each said front lip is inclined at an angle between 135 and 175 degrees inclusive to said planar surface to deflect air flow to each said ductway.

10. The device of claim 9 in which the angles of said back lips are substantially uniform, all said receiving means are of substantially equal front-to-back dimension, and each of said receiving means is offset from one another by an angle substantially the same as the angle of said back lip.

11. A controlled circulation incubator for incubating a group of specimen containers at a constant temperature, comprising:
  an upstanding chamber enclosure including a front and rear and a top and bottom having a high heat transfer characteristic,
  a plurality of rectilinear substantially uniformly dimensioned shelves, each having a front lip portion, an intermediate planar portion, and a rear lip portion, each said front lip portion being inclined at an identical included angle within the range of from 135 to 175 degrees from the said planar portion, and each said rear lip portion of every shelf being inclined at an identical included angle of from 100 to 135 degrees fromthe said planar portion,
  a U-shaped bracket including a transverse cross member and a pair of vertical side members, said bracket having a front-to-back lateral dimension substantial in proportion to the front-to-back lateral dimensions of said shelves and a transverse dimension substantially the same as said shelves, said bracket being mounted within said enclosure with the cross member opposite the top of the enclosure, said shelves being horizontally affixed to said brackeet side members substantially uniformly spaced vertically apart at said planar portions with said front lip portions directed to the enclosure front, each shelf being set back from the shelf next below it by an angle substantially the same as the angle of said back lip, the lowermost shelf being spaced from the enclosure bottom whereby (a) there are provided a plurality of stepped ductways between adjacent shelves and a ductway between the bracket cross member and shelf next adjacent ot it, (b) the spacing and horizontal cross sectional area between the enclosure rear and the rear lip portion of each shelf progressively decreases vertically from the lowermost to the uppermost shelves to provide an upwardly tapering flow path at the rear of said enclosure in which the zone of lowest pressure in said rear flow path is located substantially adjacent the rear lip portion of the uppermost shelf, and (c) the spacing and horizontal cross-sectional area between the enclosure front and the front lip portion of each shelf progressively increases vertically from the lowermost to the uppermost shelves, demarcating a downwardly tapering front flow-path in said enclousre in which the zone of lowest pressure is located substantially adjacent the front of the lowermost shelf, heating and blowing means disposed between said lowermost shelf and the enclosed bottom for heating and blowing air upwardly in said rear flow path for return circulation over the uppermost shelf and down the front flow back thereto, each said rear lip portion having a distance between the distal margin of such rear lip portion and the intersection of the rear lip to said planar surface of the shelf sufficient with respect to the spacing between the shelves to define a slot aperture between the said distal margin and the shelf next adjacent said margin effective during air circulation to produce a zone of lower pressure at said aperture than at the ductway entrance leading thereto, whereby during circulation of air through said rear and front flow paths some of said air passing down the front flow path is deflected by said front lips into said ductways to exhaust through said slot apertures into said rear front path, and sensor means positioned in the flow path of said air remote from between said shelves for sensing the temperature of the air flowing thereby and for controlling said blower and heater means to maintain the temperature of said air constant.

12. The invention according to claim 11 wherein said plate receiving means, sidewall bracket means, blower and heater means and sensor means are enclosed in a package of a material having a high heat transfer characteristic.

13. The invention according to claim 12 wherein said package material is metal.

* * * * *